(12) United States Patent
Zhao et al.

(10) Patent No.: US 9,301,784 B2
(45) Date of Patent: Apr. 5, 2016

(54) AUTOMATIC-EXTENDING AND ANTI-ROTATION SCOLIOSIS CORRECTING SYSTEM

(76) Inventors: Sheng Zhao, Taiyuan (CN); Xiaochun Wei, Taiyuan (CN); Kai Li, Taiyuan (CN)

(*) Notice: Subject to any disclaimer, the term of this patent is extended or adjusted under 35 U.S.C. 154(b) by 403 days.

(21) Appl. No.: 13/576,207

(22) PCT Filed: Jan. 28, 2011

(86) PCT No.: PCT/CN2011/000136
§ 371 (c)(1),
(2), (4) Date: Jul. 31, 2012

(87) PCT Pub. No.: WO2011/091718
PCT Pub. Date: Aug. 4, 2011

(65) Prior Publication Data
US 2012/0310285 A1    Dec. 6, 2012

(30) Foreign Application Priority Data
Jan. 31, 2010  (CN) .......................... 2010 1 0106668

(51) Int. Cl.
*A61B 17/70*      (2006.01)
(52) U.S. Cl.
CPC .......... *A61B 17/7025* (2013.01); *A61B 17/701* (2013.01); *A61B 17/7004* (2013.01); *A61B 17/7011* (2013.01)
(58) Field of Classification Search
CPC ............. A61B 17/7004; A61B 17/701; A61B 17/7011; A61B 17/7025
USPC ......................................... 606/258–261, 264
See application file for complete search history.

(56) References Cited

U.S. PATENT DOCUMENTS

| | | | |
|---|---|---|---|
| 5,555,897 A * | 9/1996 | Lathrop et al. | ..................... 5/600 |
| 2006/0009767 A1 * | 1/2006 | Kiester | ........................... 606/61 |

(Continued)

FOREIGN PATENT DOCUMENTS

| | | |
|---|---|---|
| CN | 2528400 | 1/2003 |
| CN | 101785695 | 7/2010 |

(Continued)

OTHER PUBLICATIONS

Li et al. "A Preliminary Study on a Novel Growth Guidance Rod System for Early-Onset Scoliosis in a Sheep Model" SPINE (2015) vol. 40, No. 11, 767-772.

*Primary Examiner* — Nicholas Plionis
(74) *Attorney, Agent, or Firm* — Meyertons, Hood, Kivlin, Kowert & Goetzel, P.C.; Eric B. Meyertons

(57) ABSTRACT

A spontaneous-extending and anti-rotation scoliosis correcting system comprises pedicle screws and a plurality of correcting rods locked with the pedicle screws. Each correcting rod includes at least one sleeve and at least one inserting rod which can be inserted into the sleeve. The inner wall of the sleeve and the inserting rod are the same in shape and are in clearance fit. A positioning mechanism for restricting the relative rotation of the inserting rod with respect to the sleeve is arranged on a matching surface between the inserting rod and the sleeve. The scoliosis correcting system has the benefits of ensuring the lateral stability and the anti-rotation function for scoliosis correction; having the performance of spontaneous extending along the growth direction of the spine; and ensuring both the short-term operating effect and the long-term curative effect.

9 Claims, 6 Drawing Sheets

(56) References Cited

U.S. PATENT DOCUMENTS

| | | |
|---|---|---|
| 2006/0155279 A1 | 7/2006 | Ogilvie |
| 2006/0247627 A1* | 11/2006 | Farris ................ 606/61 |
| 2008/0045951 A1 | 2/2008 | Fanger et al. |
| 2008/0195100 A1* | 8/2008 | Capote et al. ............ 606/71 |
| 2009/0093820 A1 | 4/2009 | Trieu et al. |
| 2010/0106192 A1* | 4/2010 | Barry ................ 606/258 |

FOREIGN PATENT DOCUMENTS

| | | |
|---|---|---|
| CN | 201710447 | 1/2011 |
| CN | 201684005 | 12/2012 |

* cited by examiner

AUTOMATIC-EXTENDING AND ANTI-ROTATION SCOLIOSIS CORRECTING SYSTEM

BACKGROUND OF THE INVENTION

1. Field of the Invention

The present invention relates to an internal fixation device for treating scoliosis, and particularly, to a spontaneous-extending and anti-rotation scoliosis correcting system.

2. Description of the Relevant Art

Many adolescents seriously suffering from scoliosis need surgical corrections. Currently, pedicle screw-rod systems are often used in the surgical treatment. These existing fixing technologies have the following deficiencies and disadvantages.

1. For most pedicle screw-rod systems, after the scoliosis is corrected and fixed, the shape and length of the pedicle screw-rod systems cannot be adjusted. Although the scoliosis is effectively corrected, the restriction of the fixed segment, imposed by the internal fixation of the pedicle screw-rod system, leads to an arrest of growth of the spine. Since most patients being treated for scoliosis are adolescents, and their spines continuously grow, a crankshaft phenomenon occurs in which the growth of the spines near the fixed segment is distorted and deformed, and the patients' growth is seriously impacted. If the pedicle screw-rod system is removed early, the scoliosis may reappear. So it is clinically desired that a pedicle screw-rod internal fixing system should be able to spontaneously extend along with the growth of the spine.

2. Chinese patent No. 200510086711.6 discloses a extending rod system, wherein the extending rod is an integral structure slidably connected to a plurality of pedicle screws. In this system, the pedicle screw and the correcting rod are relatively slidable rather than being locked with each other, thus the spine growth is not restricted by the extending rod. Although this system can correct the lateral and angular deformities, the pedicle screw can rotate by taking the correcting rod as an axial, since the pedicle screw and the correcting rod are not locked with each other, thus the stability of the action achieved by the pedicle screw-rod system on the spine is greatly influenced, and a worse correction effect is achieved than with other pedicle screw-rod system. Particularly, the rotated vertebrae cannot be fixed, and it is ineffective to prevent the rotation deformity.

3. The prior art also proposes a growing valve system (e.g., ISOLA fixing device) that is designed to achieve both growth extension and anti-rotation. This system employs a structure similar to the traditional pedicle screw-rod system, wherein the correcting rod and the pedicle screw are locked with each other, and the correcting rod is added with a manually extendible growing valve. The design is the most advanced scoliosis correcting system at present. The design has a good anti-rotation effect, i.e., it realizes the scoliosis correction function of the common pedicle screw-rod system with a rotation stability, and partially meets the requirement of extending the internal fixing system along with the growth. However, the design still has the following serious deficiencies, which significantly influence the treatment effect and cause great pain to the patients.

a. Since manually extension is needed, the patient will need to undergo surgery every half year to expose the rod fixed on the spine, loosen the fixing screws of the growing valve, and adjust the internal fixing length. For example, with respect to the conventional ISOLA device, the surgical incision will need to be more than 25 cm to expose the internal fixing adjustment portion fixed on the spine. These procedures will result in additional damages to the patient both physiologically and financially. Furthermore, it is increases the chance of complications such as infection. Since many patients will not accept the frequent surgery, the growing valve cannot be adjusted in time, and the spine growth is influenced. It can be seen that the frequent surgical adjustment is a major deficiency for this technology.

b. The growing valve must be long enough to ensure an effective extension distance. In order to place the growing valve, the pedicle screws are fixed in an interval of multiple vertebrae. But the span increases with the interval, and the correction effect becomes poorer. In addition, large stresses may be caused at the upper and lower pedicle screws of the growing valve. This causes the screws or rods are to be easily fractured.

c. The normal spine continuously grows and requires the internal fixation to gradually extend rather than periodically extending. Thus the traditional growing valve system does not meet the physiological requirement of the spine growth. Furthermore, the single adjustment range at each time is very limited, thereby requiring frequent adjustment.

d. An extra-long linear growing valve may influence the spine shape, and may cause a "flat back" deformity of some spines.

In order to improve the system, Chinese patent No. 200510011913.4 modifies the growing valve system by adding a rack and a drive gear. Those devices may be reached via a small incision, and the whole correcting rod may be extended by rotating the drive gear. This method shortens the surgical incision and reduces the damage during the surgeries, but still cannot avoid the need for surgery every half year. Meanwhile, the drive gear, etc. has large gaps. Connective tissues may grow into those gaps, which could increase the risk of mechanical structure failure and surgery. In conclusion, there is a definite unmet clinical need to provide an internal fixing system capable of: correcting scoliosis and preventing rotation; is naturally extendible along with the growth of the spine without any surgery; is short-segment fixable; and is multi-segment extendible without influencing the local spine shape.

SUMMARY OF THE INVENTION

Embodiments described herein break through the bottleneck of the prior art, i.e., solve the problem that the current spine correcting devices cannot be adjusted with the spine growth, or when adjustable are painful to the patients. Embodiments described herein provide a scoliosis correcting system that is: capable of correcting scoliosis and preventing rotation; is extendible with spinal growth without any surgery; has a short-segment that is fixed to the spine; does not requiring deliberately expanding the interval between the pedicle screws; and does not influencing the local spine shape.

Embodiments are implemented through the following technical solutions:

A spontaneous-extending and anti-rotation scoliosis correcting system, comprises a pedicle screw and a plurality of correcting rods locked with the pedicle screw, wherein the correcting rod includes at least one sleeve and at least one inserting rod which can be inserted into the sleeve, an inner wall of the sleeve and the inserting rod are the same in shape and are in clearance fit, a positioning mechanism for restricting the relative rotation of the inserting rod with respect to the sleeve is arranged on a matching surface between the inserting rod and the sleeve. A set of combinations of the sleeve and the inserting rod are arranged between two adjacent pedicle screws.

The positioning mechanism is composed of at least one positioning platform on the inserting rod and at least one corresponding platform on the inner wall of the sleeve. Or, the positioning mechanism is composed of at least one positioning boss on the inserting rod and at least one corresponding groove on the inner wall of the sleeve. Or, the inserting rod and the inner wall of the sleeve are mated each other with special-shaped structures, such as polygon, ellipse, etc.

The sleeve is composed of a sleeve segment on one side and a rod segment on the other side and is positioned at the end of the correcting rod. Or, the sleeve is composed of sleeve segments on two sides and a rod segment in the middle. The inserting rod is composed of a rod segment at one end and an inserting rod segment at the other end and is positioned at the end of the correcting rod. Or, the inserting rod is composed of a rod segment in the middle and inserting rod segments at two ends. Or, the sleeve and the inserting rod are integrally connected to each other, and comprise a sleeve segment at one end and an inserting rod segment at the other end, the sleeve segment and the inserting rod segment being connected via a rod segment.

Various basic structures of the sleeve and the inserting rod may be combined with one another to form the parts that can be combined with each other. Those parts may have different lengths to form different models of sleeves and inserting rods, thereby allowing the construction of correcting rods of different lengths for the patients of different ages and surgical procedures. Any region can be pre-bent, except for the sleeve segment and the inserting rod segment to be inserted into the sleeve, to fit the spinal deformity.

The method is substantially similar as that used for the conventional pedicle screw-rod system, i.e., combining the correcting rods of proper specifications, prebending them to fit the spinal deformity, connecting them with the pedicle screws without being locked, rotating the rods 90° to correct the scoliosis deformity, and then locking the rods with the pedicle screws so that they are integrally connected to each other.

Although the correcting rod is composed of a plurality of segments, the sleeve segment and the inserting rod segment at the joint of each segment will not rotate. Thus the correcting rod is stably rotatable and extendible in the longitudinal direction, and the growing of spinal will not be restricted. In addition, the plurality of sleeves can ensure a large range of extendibility, so that the correcting rod will not be easily pulled out during spinal growth.

In the traditional pedicle screw-rod system, generally every 3 or 4 vertebrae use one set of pedicle screws, and the sleeve may have a length 1 to 1.5 times that of the vertebrae. Thus the pedicle screws can be arranged in the conventional method, so as to avoid deliberately expanding the interval between the pedicle screws for the purpose of disposing an extending device when the current growing valve system is used, thereby not only ensuring the correction effect, but also preventing rod or screw fracture to occur due to concentrated stresses.

The correcting rod linear structure is only limited to the sleeves and the length is very small at each sleeve. Thus the local spine curvature is unlikely to be influenced, and as compared with prior art growing valve systems, the flat back deformity of the local spine does not occur.

In conclusion, as compared with the prior art, the present invention has the following benefits:

1. solving the difficulty of simultaneously achieving the stability and spontaneous extendibility of the spine internal fixing system, thereby ensuring not only the lateral stability and anti-rotation function required by the scoliosis correction, but also the spontaneous extendibility in the spine growth direction;

2. ensuring the short-term surgery effect and the long-term curative effect, dispelling the technical prejudice that the non-fusion scoliosis surgery cannot be completed once, greatly relieving the pain of the patients, and breaking through the traditional scoliosis treatment;

3. the pedicle screws can be arranged in a conventional method, thereby preventing rod or screw fracture due to concentrated stresses;

4. the length is very small for each sleeve, thus flat back deformity of the local spine does not occur.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
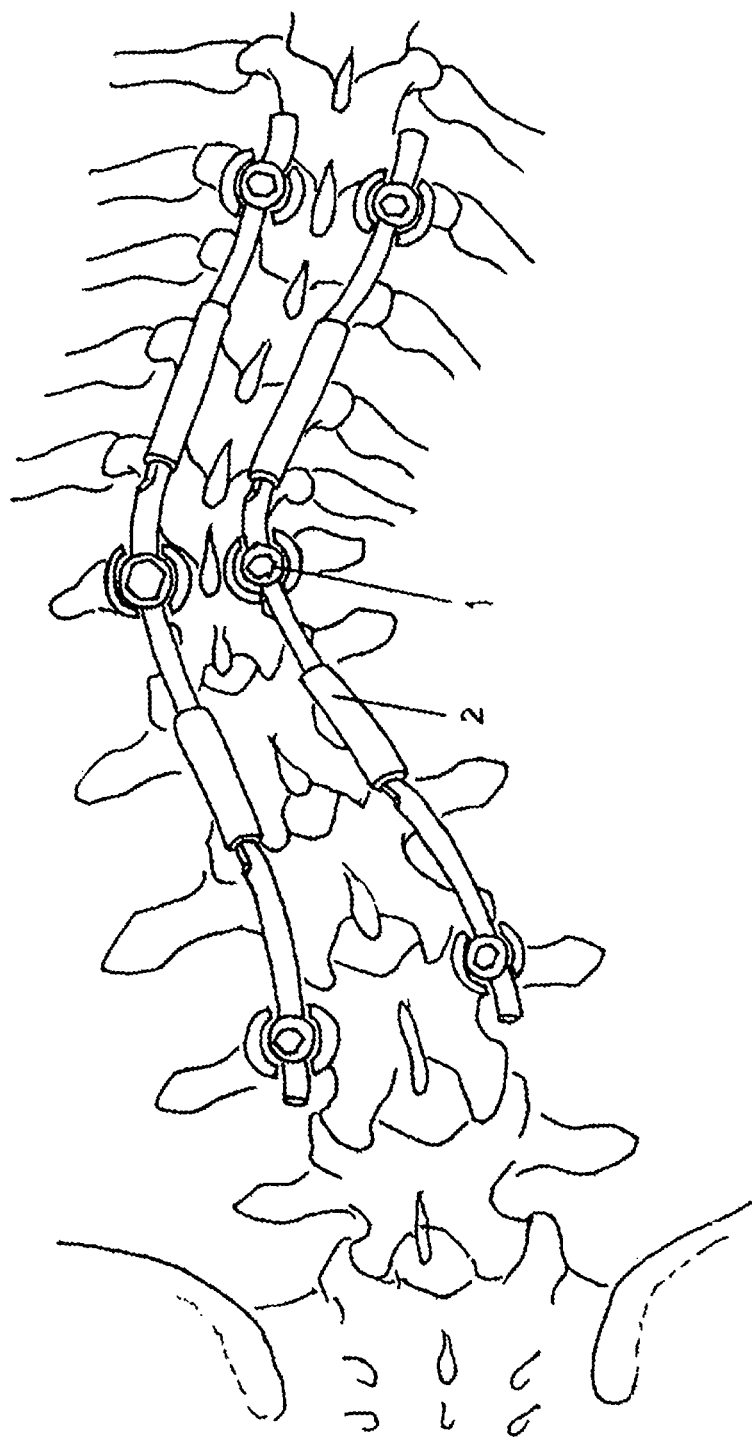
FIG. 1 is a schematic diagram of correcting system before rotating the correcting rod.
Figure 2:
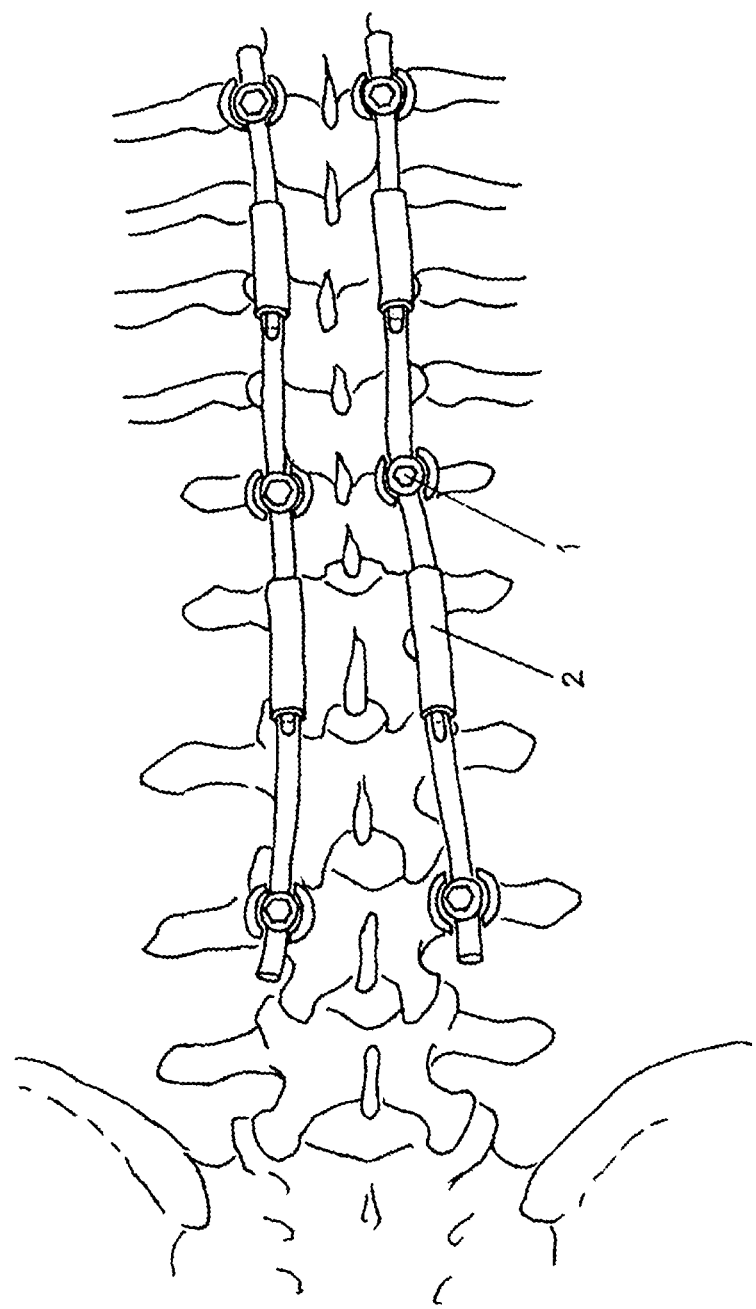
FIG. 2 is a schematic diagram of correcting system after correction by rotating the correcting rod.
Figure 3:
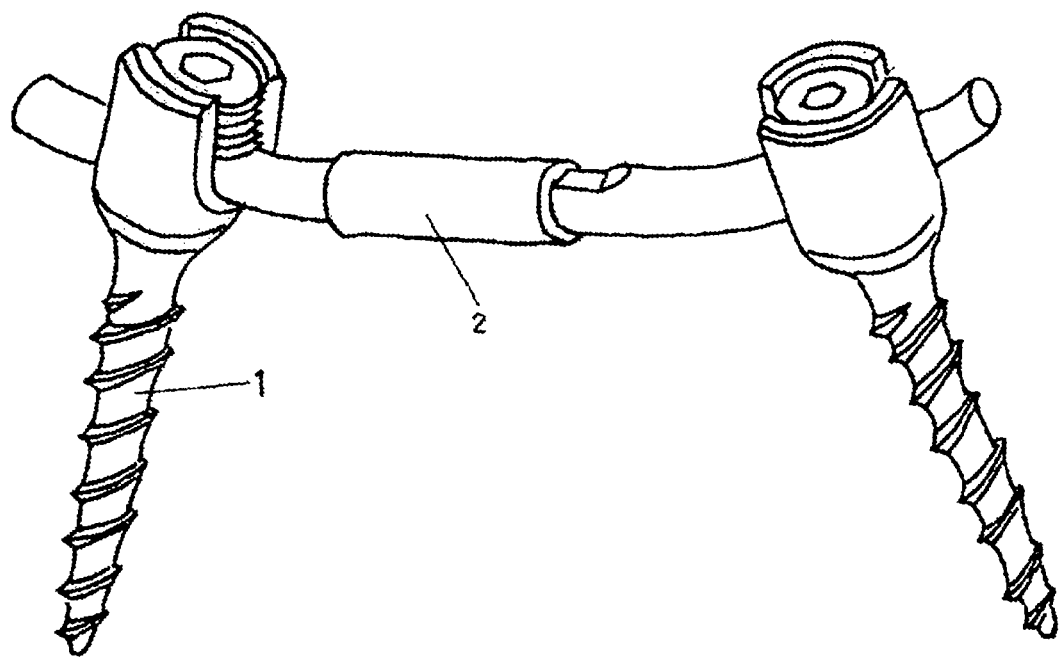
FIG. 3 is a schematic diagram of a single pedicle screw-rod before rotating the correcting rod.
Figure 4:
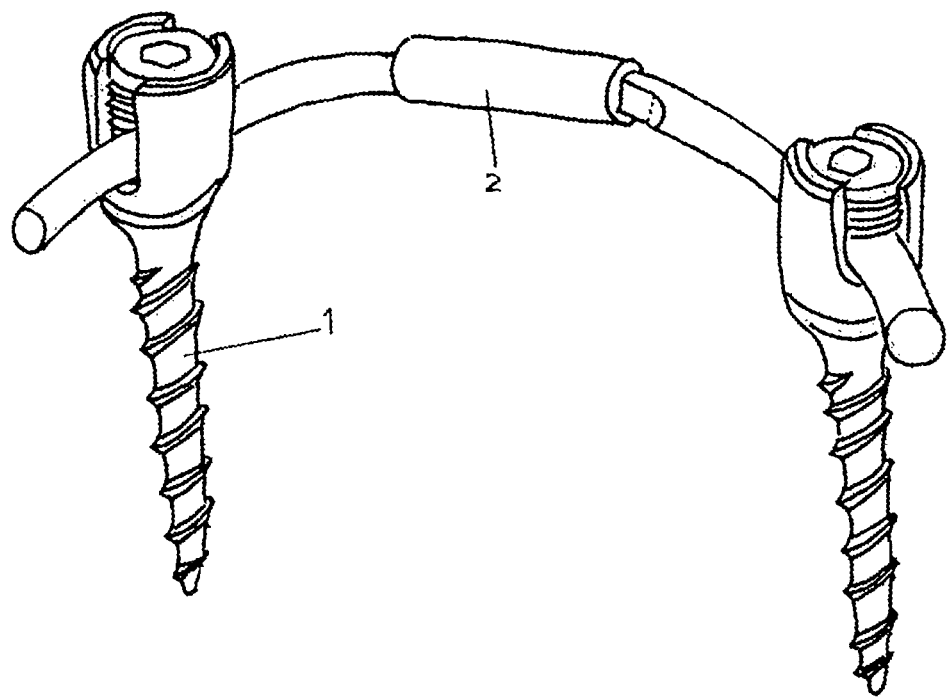
FIG. 4 is a schematic diagram of a single pedicle screw-rod after correction by rotating the correcting rod.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

The embodiments are further described in conjunction with the drawings.

Figure 6:
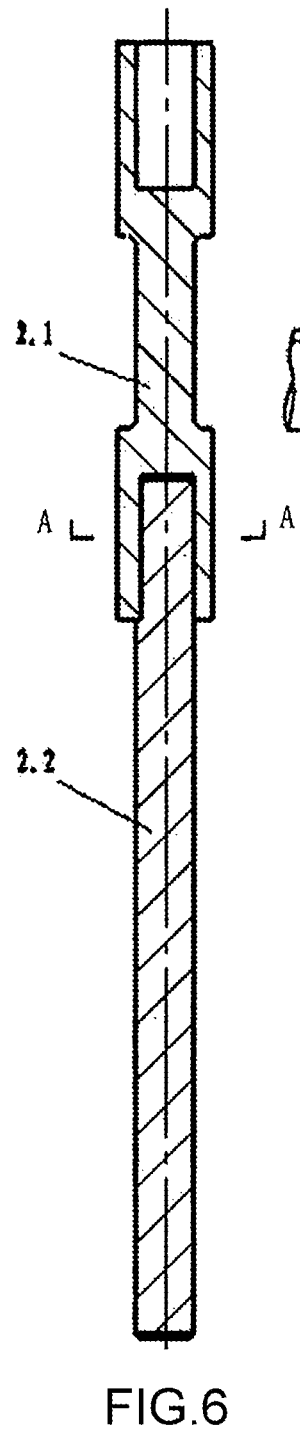
FIG. 6 is a cross-section diagram of a correcting rod.
Figure 5:
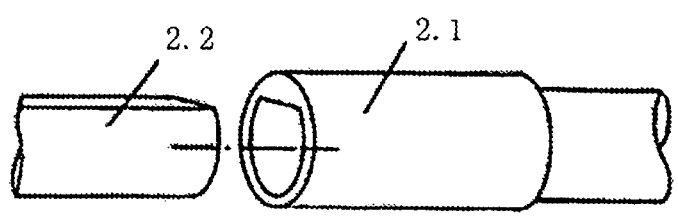
FIG. 5 is a schematic diagram of a correcting rod.

A spontaneous-extending and anti-rotation scoliosis correcting system comprises a pedicle screw 1 and correcting rods 2 locked with the pedicle screw 1, as shown in FIGS. 1 to 4. As shown in FIGS. 5 and 6, the correcting rod 2 includes at least one sleeve 2.1 and at least one inserting rod 2.2 which can be inserted into the sleeve 2.1, the inner wall of the sleeve 2.1 and the inserting rod 2.2 are the same in shape and are in clearance fit, and a positioning mechanism for restricting the relative rotation of the inserting rod 2.2 with respect to the sleeve 2.1 is arranged on the inserting rod 2.2 and the sleeve 2.1. One set of combinations of the sleeve and the inserting rod are arranged between two adjacent pedicle screws 1.

Figure 7:
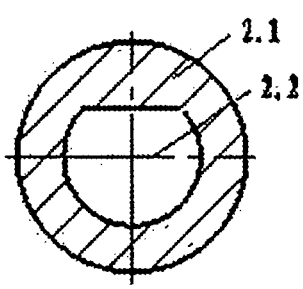
FIG. 7 is a cross-section diagram of Example 1 of a correcting rod.
Figure 8:
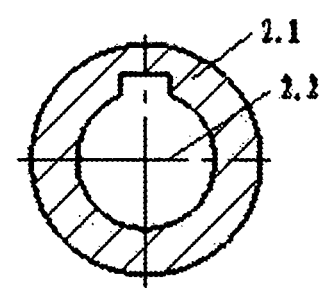
FIG. 8 is a cross-section diagram of Example 2 of a correcting rod.
Figure 9:
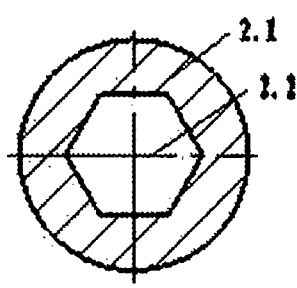
FIG. 9 is a cross-section diagram of Example 3 of a correcting rod.
Figure 10:
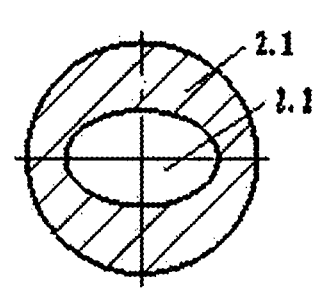
FIG. 10 is a cross-section diagram of Example 4 of a correcting rod.

The positioning mechanism is composed of at least one positioning platform on the inserting rod 2.2 and at least one corresponding platform on the inner wall of the sleeve 2.1, as shown in FIG. 7. Or, the positioning mechanism is composed of at least one positioning boss on the inserting rod 2.2 and at least one corresponding groove on the inner wall of the sleeve 2.1, as shown in FIG. 8. Or, the inserting rod 2.2 and the sleeve 2.1 are mated each other with a special-shaped structure, such as polygon, ellipse, etc, as shown in FIGS. 9 and 10.

Figure 11:
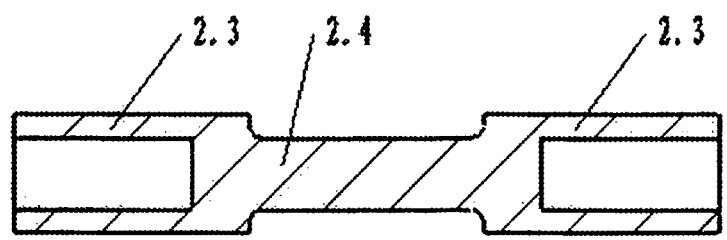
FIG. 11 is a structure diagram of a sleeve.
Figure 12:
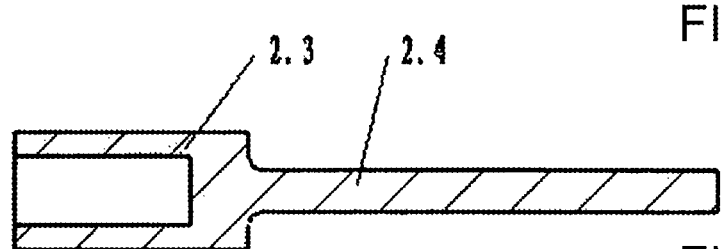
FIG. 12 is another structure diagram of a sleeve.
Figure 13:
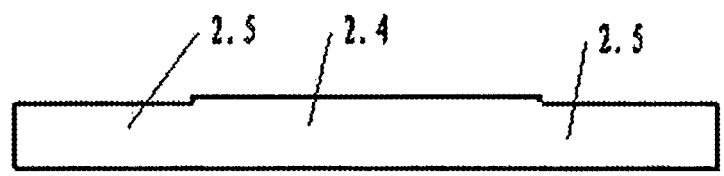
FIG. 13 is a structure diagram of an inserting rod.
Figure 14:
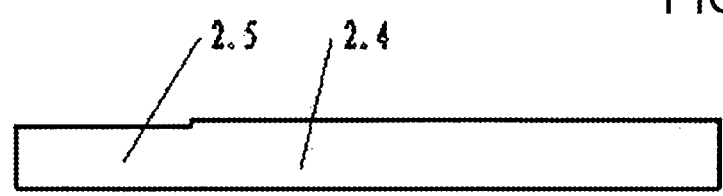
FIG. 14 is another structure diagram of an inserting rod.
Figure 15:
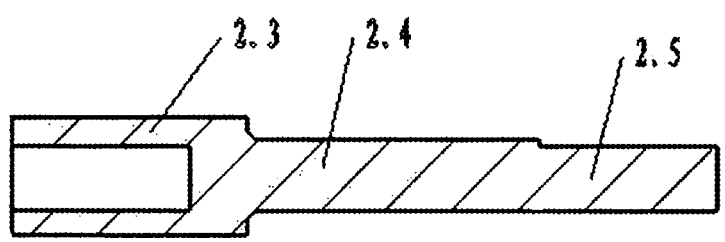
FIG. 15 is a structure diagram of integrated inserting rod and sleeve.

The sleeve 2.1 is composed of a sleeve segment 2.3 on one side and a rod segment 2.4 on the other side and used at the end of the correcting rod, as shown in FIG. 12. Or, the sleeve 2.1 is composed of sleeve segments 2.3 on two sides and a rod segment 2.4 in the middle, as shown in FIG. 11. The inserting rod 2.2 is composed of a rod segment 2.4 at one end and an inserting rod segment 2.5 at the other end, which is used at the end of the correcting rod, as shown in FIG. 14. Or, the inserting rod 2.2 is composed of a rod segment 2.4 in the middle and inserting rod segments 2.5 at two ends, as shown in FIG. 13. Or, the sleeve and the inserting rod are integrally connected to each other, and comprise a sleeve segment 2.3 at one end and an inserting rod segment 2.5 at the other end, the sleeve segment 2.3 and the inserting rod segment 2.5 being connected via a rod segment 2.4, as shown in FIG. 15.

Various basic structures of the sleeve and the inserting rod may be combined to form parts that can be combined with each other. Those parts may have different lengths to form different models of sleeves and inserting rods, thereby constructing the correcting rods of different lengths for the patients of different ages and surgical procedures. Any region can be pre-bent except the sleeve segment and the inserting rod segment to be inserted into the sleeve, so as to fit the spinal deformity.

The method used by the present invention is substantially the same as that used for the conventional pedicle screw-rod system, i.e., combining the correcting rods of proper specifications, prebending them to fit the spinal deformity, connecting them with the pedicle screws without being locked, rotating the correcting rods 90° to correct the scoliosis deformity, and then locking the correcting rods with the pedicle screws so that they are integrally connected to each other.

What is claimed is:

1. A spontaneous-extending and anti-rotation scoliosis correcting system, comprising:
    pedicle screws; and
    a plurality of connecting rods locked with the pedicle screws, wherein at least one of the plurality of connecting rods comprises:
        at least one sleeve;
        at least one inserting rod which can be inserted into the sleeve, wherein an inner wall of the sleeve and the inserting rod are the same in shape and are in clearance fit, wherein at least a portion of the inserting rod is non-circular and
        a positioning mechanism having a non-circular portion which is complementary to the non-circular portion of the inserting rod, wherein the positioning mechanism restricts the relative rotation of the inserting rod with respect to the sleeve when arranged in the sleeve;
    wherein a portion of at least one of the plurality of connecting rods is configured to be disposed in a pedicle screw, and wherein the portion of at least one of the plurality of connecting rods disposed in the pedicle screw has a circular cross-section which allows the connecting rod to be rotated with respect to the pedicle screw;
    and wherein the sleeve allows substantially unrestricted movement of the inserting rod within the sleeve in a longitudinal direction, wherein the unrestricted movement of the inserting rod allows unrestricted shortening and lengthening of the distance between the pedicle screws.

2. The spontaneous-extending and anti-rotation scoliosis correcting system according to claim 1, wherein the positioning mechanism is composed of at least one positioning platform on the inserting rod and at least one corresponding platform on the inner wall of the sleeve.

3. The spontaneous-extending and anti-rotation scoliosis correcting system according to claim 1, wherein the positioning mechanism is composed of at least one positioning boss on the inserting rod and at least one corresponding groove on the inner wall of the sleeve.

4. The spontaneous-extending and anti-rotation scoliosis correcting system according to claim 1, wherein the positioning mechanism is the inserting rod and the sleeve with a mated complimentary-shaped structure.

5. The spontaneous-extending and anti-rotation scoliosis correcting system according to claim 1, wherein the sleeve is composed of a sleeve segment on one side and a rod segment on the other side.

6. The spontaneous-extending and anti-rotation scoliosis correcting system according to claim 1, wherein the sleeve is composed of sleeve segments on two sides and a rod segment in the middle.

7. The spontaneous-extending and anti-rotation scoliosis correcting system according to claim 1, wherein the inserting rod is composed of a rod segment at one end and an inserting rod segment at the other end.

8. The spontaneous-extending and anti-rotation scoliosis correcting system according to claim 1, wherein the inserting rod is composed of a rod segment in the middle and inserting rod segments at two ends.

9. The spontaneous-extending and anti-rotation scoliosis correcting system according to claim 1, wherein at least one of the sleeves and at least one of the inserting rods are integrally connected to each other, wherein the integrally connected sleeve and inserting rod comprise; a rod segment; a sleeve segment coupled to the rod segment; and an inserting rod segment coupled to the other end of the rod segment; and wherein the inserting rod segment is insertable into the sleeve of another one of the plurality of connecting rods.

* * * * *